(12) United States Patent
Melson et al.

(10) Patent No.: US 8,647,429 B2
(45) Date of Patent: Feb. 11, 2014

(54) EFFECT PIGMENTS

(75) Inventors: Sabine Melson, Muehltal (DE); Volker Wilhelm, Lorsch (DE); Ulrich Schoenefeld, Bickenbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/577,026

(22) PCT Filed: Feb. 2, 2011

(86) PCT No.: PCT/EP2011/000464
§ 371 (c)(1),
(2), (4) Date: Aug. 3, 2012

(87) PCT Pub. No.: WO2011/095326
PCT Pub. Date: Aug. 11, 2011

(65) Prior Publication Data
US 2012/0308667 A1  Dec. 6, 2012

(30) Foreign Application Priority Data
Feb. 4, 2010  (EP) .................................... 10001163

(51) Int. Cl.
*C09C 1/00*   (2006.01)
*C09C 3/06*   (2006.01)

(52) U.S. Cl.
USPC ........... 106/415; 106/417; 106/426; 106/427; 106/428; 106/436; 106/442; 106/444; 106/446; 427/218

(58) Field of Classification Search
USPC ......... 106/442, 444, 446, 415, 417, 426, 427, 106/428, 436, 31.9; 427/218
See application file for complete search history.

(56) References Cited

U.S. PATENT DOCUMENTS

| | | |
|---|---|---|
| 3,874,890 A | 4/1975 | Bernhard et al. |
| 3,926,659 A | 12/1975 | Bernhard et al. |
| 4,456,486 A | 6/1984 | Bernhard et al. |
| 4,457,784 A | 7/1984 | Bernhard et al. |
| 4,482,389 A | 11/1984 | Franz et al. |
| 4,494,993 A | 1/1985 | Bernhard et al. |
| 4,509,988 A | 4/1985 | Bernhard et al. |
| 4,537,636 A | 8/1985 | Bernhard et al. |
| 5,456,749 A | 10/1995 | Iwasa et al. |
| 6,176,918 B1 | 1/2001 | Glausch et al. |
| 6,706,330 B2 * | 3/2004 | Takahashi et al. ......... 427/419.2 |
| 6,875,264 B2 * | 4/2005 | Zimmermann et al. ...... 106/446 |
| 7,226,503 B2 * | 6/2007 | Anselmann et al. .......... 106/489 |
| 7,455,726 B2 | 11/2008 | Schoenefeld et al. |
| 7,993,444 B2 * | 8/2011 | Fuller et al. .................... 106/436 |
| 8,007,583 B2 * | 8/2011 | Fuller et al. .................... 106/446 |
| 8,088,214 B2 * | 1/2012 | Fuller et al. .................... 106/436 |
| 8,282,729 B2 * | 10/2012 | Fuller et al. .................... 106/436 |

FOREIGN PATENT DOCUMENTS

| | | |
|---|---|---|
| CA | 957 108 | 11/1974 |
| DE | 14 67 468 | 12/1968 |
| DE | 15 22 572 | 9/1969 |
| DE | 19 59 988 | 6/1971 |
| DE | 20 09 566 | 11/1971 |
| DE | 22 14 545 | 10/1972 |
| DE | 22 15 191 | 10/1972 |
| DE | 22 44 298 | 3/1974 |
| DE | 23 13 331 | 9/1974 |
| DE | 31 37 808 | 3/1983 |
| DE | 31 37 809 | 3/1983 |
| DE | 31 51 354 | 7/1983 |
| DE | 31 51 355 | 7/1983 |
| DE | 32 11 602 | 10/1983 |
| DE | 32 35 017 | 3/1984 |
| DE | 196 39 783 | 4/1998 |
| EP | 0 644 242 | 3/1995 |
| GB | 974 874 | 11/1964 |
| GB | 1 287 225 | 8/1972 |
| GB | 1 359 933 | 7/1974 |
| WO | WO-98 13426 | 4/1998 |
| WO | WO-94 01498 | 1/2004 |
| WO | WO-2004 104110 | 12/2004 |

OTHER PUBLICATIONS

Merck KGaA, "Optically variable pigments in plastics and plastics articles," Research Disclosure Database No. 472005, Aug. 2003.
Rüger, R. Dr., "Cosmetic Formulations containing Special Effect pigments," Research Disclosure Database No. 471001, Jul. 2003.
International Search Report for PCT/EP2011/000464 dated Apr. 6, 2011.

* cited by examiner

*Primary Examiner* — Anthony J Green
(74) *Attorney, Agent, or Firm* — Millen, White, Zelano & Branigan, P.C.

(57) ABSTRACT

The present invention relates to effect pigments based on uncoated or coated flake-form substrates having an outer coating comprising a) $TiO_2$ and b) $Al_2O_3$, MgO and/or CaO and c) $SiO_2$ and d) ZnO and/or e) at least one mixed oxide of the elements mentioned under a) to d), and to the use thereof, inter alia in paints, coatings, printing inks, plastics and cosmetic formulations.

21 Claims, No Drawings

EFFECT PIGMENTS

The present invention relates to effect pigments based on uncoated or coated flake-form substrates having an outer coating comprising a) $TiO_2$ and b) $Al_2O_3$, MgO and/or CaO, and c) $SiO_2$ and d) ZnO and/or e) at least one mixed oxide of the elements mentioned under a), b), c) and d), and to the use thereof, inter alia in paints, coatings, printing inks, plastics and cosmetic formulations.

Pigments comprising one or more layers comprising an oxide and/or hydroxide of a transition-metal compound, such as, for example, $TiO_2$, $Fe_2O_3$, etc., or mixtures of the oxides, as described, for example, in WO 2008/048922, WO 2006/0181096, EP 0882099 and EP 1422268, are employed as lustre or effect pigments in many areas of industry, in particular in decorative coating, in plastics, paints, coatings, printing inks and in cosmetic formulations. In order to improve their properties, the application media generally comprise a number of additives, such as, for example, plasticisers, fillers, stabilisers, anti-ageing agents, lubricants and release agents, antistatics and colorants.

Pigments are employed indoors and outdoors. Outdoor application, in particular, makes high demands of a pigment. Various factors, such as exposure to light, high atmospheric humidity, high and low temperatures, occur here which act on the pigment. In particular, plastic parts and paint coats for outdoor applications are often subjected to extreme weathering conditions and long-lasting intense exposure to light over an extended time, which results in ageing of the materials. This is evident in discolorations, embrittlement and reduced mechanical and chemical stability. An undesired interaction is frequently observed, in particular, between the effect pigments on the one hand and additives in the application medium on the other hand, presumably arising through transition-metal cations reacting with the organic-based additives. Thus, it is frequently observed in plastics that the stabiliser and/or ageing agent molecules diffuse to the surface of the pigment particles, where they result in a yellowing reaction, which often also takes place in the dark, in particular if the plastics comprise phenolic components as antioxidants, thermal stabilisers or UV stabilisers.

In order to inhibit these ageing processes, stabilisers, for example UV light-absorbing substances, are added to formulations for outdoor applications. In addition, the pigments may be provided with further layers, so-called after-coatings. Thus, EP 0 644 242 describes polyolefin compositions comprising titanium dioxide-coated mica particles which are coated with one or more layers of $SiO_2$ and $Al_2O_3$ and are calcined. In addition, the composition comprises an antioxidant in order to prevent yellowing. WO 1994/001498 discloses $TiO_2$ pigments which, in order to prevent yellowing, are provided with a layer of silicon oxide and/or silicon oxide hydrate on a preferably calcined $TiO_2$ layer, with a layer of aluminium oxide and/or aluminium oxide hydrate on this silicon-containing layer and with a layer of zinc oxide and/or zinc oxide hydrate on this aluminium-containing layer.

The aftercoatings often also comprise organic components. The organic components are preferably used for protection against moisture. If an aftercoated pigment of this type is sent to the process of plastics processing, the pigment is in some cases heated at up to 300° C. This temperature damages the organic part, so that, for example, yellowing already occurs during processing or adequate resistance against UV irradiation is not provided.

The current solutions cover some of the demands made of effect pigments, but not the totality of the demands. In addition, the known methods for the stabilisation of effect pigments all require additional process steps for application of the requisite aftercoatings. There is thus a demand for further improvements, and the object was to provide effect pigments which are light-stable without having the said disadvantages.

Surprisingly, it has now been found that this object is achieved by the effect pigments according to the invention. The present invention therefore relates to effect pigments based on uncoated, flake-form substrates or flake-form substrates coated with one or more metal oxides, which are distinguished by the fact that they have an outer metal oxide-containing, calcined coating comprising a) $TiO_2$ and b) $Al_2O_3$, MgO and/or CaO, and c) $SiO_2$ and d) ZnO and/or e) at least one mixed oxide of the elements mentioned under a), b), c) and d). The outer metal oxide-containing, calcined coating preferably consists of a) $TiO_2$ and b) $Al_2O_3$, MgO and/or CaO, and c) $SiO_2$ and d) ZnO and/or at least one mixed oxide of these elements. In particular, the outer metal oxide-containing, calcined coating consists of $TiO_2$ and $Al_2O_3$ or CaO and $SiO_2$ and ZnO and/or at least one mixed oxide of these elements. The outer metal oxide-containing, calcined coating particularly preferably consists of $TiO_2$ and $Al_2O_3$ and $SiO_2$ and ZnO and/or at least one mixed oxide of these elements.

The outer metal oxide-containing, calcined coating according to the invention, also called outer coating below, is located on one or more sides of the substrates. The outer coating according to the invention preferably envelops the substrates. This outer coating preferably has a distribution of the oxides and/or mixed oxides in which the concentration of $TiO_2$ is the highest in the vicinity of the substrate and drops towards the pigment surface. The further oxides according to the invention can be uniformly distributed in the coating here. Decreasing or increasing concentrations of individual or all oxides, starting from the pigment surface, may preferably be present, where the outer coating preferably comprises the Al, Mg, Ca, Si and Zn oxides and/or mixed oxides predominantly in the outer region. The outer coating here comprises, in particular, $Al_2O_3$ (and/or MgO and/or CaO), $SiO_2$ and/or ZnO in the outer region. The outer coating preferably comprises Al, Si and Zn oxides and/or mixed oxides predominantly in the outer region. The concentration of $SiO_2$ and/or ZnO, in particular of ZnO, is preferably the greatest in the outer edge region of the coating. In a particularly preferred embodiment of the invention, the outer coating has the highest concentration of $TiO_2$, alone or in a mixture with $Al_2O_3$, in the vicinity of the substrate.

The oxides which are essential to the invention and are mentioned under a) to d) may also be in the form of one or more mixed oxides or in the form of a mixture of mixed oxides and oxides. Oxides in the sense of the invention also include silicates. The effect pigments preferably comprise zinc in the form of the oxide or mixed oxide in the following amounts in the outer coating, indicated as ZnO and based on the total weight of the calcined pigment: ≥0.5% by weight, preferably 0.5-10% by weight, in particular 0.8-5% by weight or 1.0-5% by weight, of ZnO. The effect pigments preferably comprise aluminium, magnesium and/or calcium in the form of the oxide or mixed oxide in the following amounts in the outer coating, indicated as $Al_2O_3$, MgO or CaO respectively and based on the total weight of the calcined pigment: ≥0.1% by weight, preferably 0.1-6% by weight, in particular 0.5-6% by weight or 0.5-3% by weight, of $Al_2O_3$, MgO and/or CaO respectively. Preference is given to effect pigments in which the total amount of $Al_2O_3$, MgO and/or CaO is in the percent by weight ranges indicated. The effect pigments preferably comprise silicon in the form of the oxide or mixed oxide in the following amounts in the outer coating, indicated as $SiO_2$ and based on the total weight of the calcined pigment: ≥1.5% by weight, preferably 1.5-10% by weight, in particular 2.5-6% by weight, of $SiO_2$.

The effect pigments particularly preferably comprise 0.5% by weight, of ZnO and ≥0.1% by weight of $Al_2O_3$ or CaO, preferably $Al_2O_3$, and ≥1.5,% by weight of $SiO_2$ in the outer coating, based on the total weight of the calcined pigment. The effect pigments especially preferably comprise 0.5-10% by weight of ZnO and 0.1-6% by weight of $Al_2O_3$ or CaO, preferably $Al_2O_3$, and 1.5-10% by weight of $SiO_2$ in the outer coating, based on the total weight of the calcined pigment. Effect pigments having an outer coating comprising 0.8-5% by weight of ZnO and 0.5-6% by weight of $Al_2O_3$ and 2.5-6% by weight of $SiO_2$, based on the total weight of the calcined pigment, are particularly advantageous. Effect pigments having an outer coating comprising 1.0-5% by weight, in particular 1.0-2% by weight, of ZnO and 0.5-3% by weight, in particular 1-3% by weight, of $Al_2O_3$ and 2.5-6% by weight, in particular 2.5-4% by weight, of $SiO_2$, based on the total weight of the calcined pigment, are especially particularly advantageous. The weight ratio of ZnO to $Al_2O_3$ is preferably equal to 0.1-10, preferably 0.3-10 or 0.4-10, preferably 0.3-8, in particular 0.3-2. The $SiO_2/ZnO$ weight ratio is preferably equal to 0.1-6, in particular 0.2-5, preferably 2-4.5. In an embodiment of the invention, the $SiO_2/ZnO$ weight ratio can also be equal to 0.4-2.0, preferably 0.8-1.2.

The effect pigments preferably comprise ≥20% by weight of $TiO_2$ in the outer coating, based on the total weight of the calcined pigment, where the precise $TiO_2$ content is dependent on the desired interference colour, and the adjustment is familiar to the person skilled in the art. The effect pigments furthermore preferably comprise 20% by weight of $TiO_2$, ≥0.5% by weight of ZnO, ≥0.1% by weight of $Al_2O_3$ and ≥1.5% by weight of $SiO_2$ in the outer coating, based on the total weight of the calcined pigment. Effect pigments having an outer coating consisting of ≥20% by weight of $TiO_2$ and 1.0-5% by weight, in particular 1.0-2% by weight, of ZnO and 0.5-3% by weight, in particular 1-3% by weight, of $Al_2O_3$, and 2.5-6% by weight, in particular 2.5-4% by weight, of $SiO_2$, based on the total weight of the calcined pigment, are especially particularly advantageous.

The outer coating of the calcined pigment usually has a thickness of >50 nm, preferably >65 nm, in particular >80 nm. The outer coating here is thicker than it would be physically and theoretically for achieving the desired interference colour. The thickness of the outer coating is preferably ≥20%, preferably ≥40%, more than the physical layer thickness of the corresponding interference colour. 50-80% more are particularly preferred. However, outer coatings having a thickness of >100% more than the physical layer thickness are also possible. In principle, precise adjustment and control of the layer thickness in the nanometre range is known to the person skilled in the art for achieving a certain interference colour (Gerhard Pfaff, Spezielle Effektpigmente [Specific Effect Pigments], Vincentzverlag, FIG. 2.25 and FIG. 2.26; pages 50-53). A silver-white pigment based on $TiO_2$ has a $TiO_2$ layer with a thickness of about 50 nm in accordance with physical laws. By contrast, the outer coating according to the invention of a silver-white pigment can be up to 120 nm thick. The outer coating according to the invention of an interference gold can be up to 150 nm thick. Other interference colours exhibit corresponding layer thicknesses. A conventional blue interference layer is about 120 nm thick, an outer coating according to the invention can be, by contrast, 10-100 nm thicker.

It is particularly advantageous for the effect pigments according to the invention to have a specific surface area of ≤4 $m^2/g$, preferably ≤3 $m^2/g$, measured by the BET method (DIN ISO 9277: 2003-05). The specific surface areas of pigments according to the invention and those of the prior art (in each case calcined at 750° C.) differ, for example, as follows:
a) Mica of fraction 5-25 µm having a calcined $TiO_2$ layer exhibits a surface area of 7.9 $m^2/g$.
b) Mica of fraction 5-25 µm having a calcined outer coating according to the invention exhibits a surface area of 2.4 $m^2/g$.
c) Mica 10-60 µm having a calcined $TiO_2$ layer exhibits a surface area of 6.5 $m^2/g$.
d) Mica 10-60 µm having a calcined outer coating according to the invention exhibits, for example, a surface area of 2.0-2.4 $m^2/g$.

The effect pigments according to the invention preferably exhibit a reduction in the surface area of 30-80%, preferably ≥40%, particularly preferably 40-65%, compared with a pigment comprising a calcined $TiO_2$ layer as outer layer.

In particular, effect pigments having an outer coating consisting of ≥20% by weight of $TiO_2$ and 1.0-5% by weight, in particular 1.0-2% by weight, of ZnO and 0.5-3% by weight, in particular 1-3% by weight, of $Al_2O_3$, and 2.5-6% by weight, in particular 2.5-4% by weight, of $SiO_2$, based on the total weight of the calcined pigment, with a thickness of the outer coating of ≥40%, preferably 50-80%, more than the physical layer thickness of the corresponding interference colour and a specific surface area of ≤3 $m^2/g$, measured by the BET method, are particularly advantageous.

Suitable substrates for the effect pigments according to the invention are, for example, all known coated or uncoated, flake-form substrates, preferably transparent or semi-transparent flakes. Suitable are, for example, phyllosilicates, in particular synthetic or natural mica, glass flakes, metal flakes, $SiO_x$ flakes (x=≤2.0, preferably x=2), $Al_2O_3$ flakes, $TiO_2$ flakes, synthetic or natural iron oxide flakes, graphite flakes, liquid crystal polymers (LCPs), holographic pigments, BiOCl flakes or mixtures of the said flakes. The metal flakes can consist, inter alia, of aluminium, titanium, bronze, steel or silver, preferably of aluminium and/or titanium. The metal flakes here may have been passivated by corresponding treatment. Preference is given to coated or uncoated flakes of synthetic or natural mica, glass flakes, $SiO_2$ flakes and $Al_2O_3$ flakes, in particular synthetic or natural mica flakes and $SiO_2$ flakes. In an embodiment of the invention, uncoated, synthetic or natural, mica flakes are preferred.

In general, the flake-form substrates have a thickness between 0.05 and 5 µm, in particular between 0.1 and 4.5 µm. Glass flakes preferably have a thickness of ≤1 µm, in particular of ≤900 nm and very particularly preferably of ≤500 nm. The size of the substrates is not crucial per se and can be matched to the particular application. The particle size is usually 1-350 µm, preferably 2-200 µm, and in particular between 5-150 µm. In general, both coarse flakes having particle sizes of 10-200 µm, preferably of 40-200 µm, in particular of 10-130 µm, and also fine flakes having particle sizes of 1-60 µm, preferably of 5-60 µm, in particular of 10-40 µm, can be used. Substrate mixtures consist of flakes having different particle sizes can preferably also be employed. Particularly preferred substrate mixtures consist of coarse and fine flakes, in particular S mica (>125 µm) and F mica (<25 µm). The particle sizes are determined using commercially available instruments which are known to the person skilled in the art (for example from Malvern, Horiba) by means of laser diffraction on the powder or on pigment suspensions. The substrates preferably have a form factor (aspect ratio: diameter/thickness ratio) of 5-750, in particular of 10-300 and very particularly preferably of 20-200. In addition, the use of other substrates, such as, for example, spherical particles or needle-shaped substrates, which may be covered with the above-mentioned layers, is also possible.

In a further embodiment, the substrate can be coated on one or more sides with one or more transparent, semi-transparent and/or opaque layers comprising metal oxides, metal oxide hydrates, metal suboxides, metals, metal fluorides, metal nitrides, metal oxynitrides or mixtures of these materials. The substrate is preferably sheathed by these layers. The metal oxide, metal oxide hydrate, metal suboxide, metal, metal fluoride, metal nitride, metal oxynitride layers or the mixtures thereof can be of low refractive index (refractive index <1.8) or high refractive index (refractive index ≥1.8, preferably ≥2.0.). Suitable metal oxides and metal oxide hydrates are all metal oxides or metal oxide hydrates known to the person skilled in the art, such as, for example, aluminium oxide, aluminium oxide hydrate, silicon oxide, silicon oxide hydrate, iron oxide, tin oxide, cerium oxide, zinc oxide, zirconium oxide, chromium oxide, titanium oxide, in particular titanium dioxide, in the rutile or anatase modification, titanium oxide hydrate and mixtures thereof, such as, for example, ilmenite or pseudobrookite. Metal suboxides which can be employed are, for example, the titanium suboxides. Suitable metals are, for example, chromium, aluminium, nickel, silver, gold, titanium, copper or alloys, a suitable metal fluoride is, for example, magnesium fluoride. Metal nitrides or metal oxynitrides which can be employed are, for example, the nitrides or oxynitrides of the metals titanium, zirconium and/or tantalum. Metal oxide, metal, metal fluoride and/or metal oxide hydrate layers and very particularly preferably metal oxide and/or metal oxide hydrate layers are preferably applied to the substrate. Particular preference is given to oxides and/or oxide hydrates of aluminium, silicon, iron, tin and titanium, in particular titanium dioxide, in the rutile or anatase modification, preferably in the rutile modification, and mixtures of these compounds. For rutilisation of titanium dioxide, a tin dioxide layer is usually applied beneath a titanium dioxide layer. Thus, the effect pigments according to the invention may, for rutilisation of the titanium dioxide present in the outer coating which is essential to the invention, also comprise a tin dioxide layer between substrate and outer coating. Furthermore, multilayered structures comprising high- and low-refractive-index metal oxide, metal oxide hydrate, metal or metal fluoride layers may also be present, where high- and low-refractive-index layers preferably alternate. Particular preference is given to layer packages comprising a high-refractive-index layer (refractive index ≥2.0) and a low-refractive-index layer (refractive index <1.8), where one or more of these layer packages may have been applied to the substrate. The sequence of the high- and low-refractive-index layers can be matched to the substrate in order to include the substrate in the multilayered structure. In a further embodiment, the metal oxide, metal oxide hydrate, metal suboxide, metal, metal fluoride, metal nitride, metal oxynitride layers may have been mixed or doped with colorants or other elements. Suitable colorants or other elements are, for example, organic or inorganic coloured pigments, such as coloured metal oxides, for example magnetite, chromium oxide or coloured pigments, such as, for example, Berlin Blue, ultramarine, bismuth vanadate, Thenard's Blue, or alternatively organic coloured pigments, such as, for example, indigo, azo pigments, phthalocyanines or also Carmine Red, or elements, such as, for example, yttrium or antimony. Effect pigments comprising these layers exhibit high colour variety in relation to their mass tone and can in many cases exhibit an angle-dependent change in the colour (colour flop) due to interference.

The layers of metal oxides, hydroxide and/or oxide hydrates are preferably applied by wet-chemical methods, where it is possible to use the wet-chemical coating methods developed for the preparation of effect pigments, which result in sheathing of the substrate. Methods of this type are described, for example, in DE 14 67 468, DE 20 09 566, DE 22 14 545, DE 22 15 191, DE 22 44, 298, DE 23 13 331, DE 31 37 808, DE 31 37 809, DE 31 51 343, DE 31 51 354, DE 31 51 355, DE 32 11 602, DE 32 35 017 or also in further patent documents and other publications known to the person skilled in the art. Examples and embodiments of the above-mentioned materials and pigment structures can also be found, for example, in Research Disclosures RD 471001 and RD 472005.

The thickness of the individual layers on the substrate is, as is familiar to the person skilled in the art, essential for the optical properties of the pigment. The thickness of the metal oxide, metal oxide hydrate, metal suboxide, metal, metal fluoride, metal nitride, metal oxynitride layers or a mixture thereof is usually 10 to 1000 nm, preferably 15 to 800 nm, in particular 20 to 600 nm. Layer thicknesses of 20 to 200 nm are particularly suitable. The thickness of the metal layers is preferably 4 to 50 nm.

If desired for certain applications, such as, for example, specific coatings, an organic coating may additionally be applied to the outer metal oxide-containing, calcined coating which is essential to the invention, comprising a) $TiO_2$ and b) $Al_2O_3$, MgO and/or CaO, and c) $SiO_2$ and d) ZnO and/or e) at least one mixed oxide of the elements mentioned under a), b), c) and d). The organic coating has a positive influence on the surface properties of the calcined oxide layers. The surfaces provided with the organic coating are more hydrophobic and less polar than the untreated oxide surfaces and can thus be wetted better by binders and organic solvents. This results in better compatibility of the pigments according to the invention with the binder systems used in the application. Furthermore, the organic coating inhibits agglomeration of the pigment particles, owing to its steric masking of the pigment surface, and thus improves the dispersibility thereof. This organic coating can consist of coupling reagents, such as, for example, organosilanes, organoaluminates, organotitanates and/or zirconates. The coupling agents are preferably organosilanes. Examples of organosilanes are propyltrimethoxysilane, propyltriethoxysilane, iso-butyltrimethoxysilane, n-octyltrimethoxysilane, i-octyltrimethoxysilane, n-octyltriethoxysilane, n-decyltrimethoxysilane, dodecyltrimethoxysilane, hexadecyl-trimethoxysilane, vinyltrimethoxysilane, preferably n-octyltrimethoxysilane and n-octyltriethoxysilane. Suitable oligomeric, alcohol-free organosilane hydrolysates are, inter alia, the products marketed under the trade name Dynasylan® Hydrosil by Evonik Industries, such as, for example, Dynasylan® Hydrosil 2926, Dynasylan® Hydrosil 2909, Dynasylan® Hydrosil 2907, Dynasylan® Hydrosil 2781, Dynasylan® Hydrosil 2776, Dynasylan® Hydrosil 2627. In addition, oligomeric vinylsilane and also aminosilane hydrolysate is suitable as organic coating. Functionalised organosilanes are, for example, 3-aminopropyltrimethoxysilane, 3-methacryloxytrimethoxysilane, 3-glycidyloxypropyl-trimethoxysilane, beta-(3,4-epoxycyclohexyl)ethyltrimethoxysilane, gamma-isocyanatopropyltrimethoxysi lane, 1,3-bis(3-glycidoxypropyl)-1,1,3,3,-tetra-methyldisiloxane, ureidopropyltriethoxysilane, preferably 3-aminopropyl-trimethoxysilane, 3-methacryloxytrimethoxysilane, 3-glycidyloxypropyl-trimethoxysilane, beta-(3,4-epoxycyclohexyl) ethyltrimethoxysilane, gamma-isocyanatopropyltrimethoxysilane. Examples of polymeric silane systems are described in WO 98/13426 and are marketed, for example, by Evonik Industries under the trade name Dynasylan® Hydrosil. The amount of organic coating can be between 0.2 and 5% by weight, based on the pigment, preferably 0.5 to 2% by weight.

The invention furthermore relates to a process for the preparation of the effect pigments according to the invention. The outer coating according to the invention of the flake-form substrates is preferably produced by wet-chemical methods. The effect pigments are subsequently calcined. These methods are familiar to the person skilled in the art. In the case of wet-chemical application, the corresponding oxides, hydroxides and/or oxide hydrates are deposited on the substrates, with the substrates preferably being sheathed. To this end, the flake-form substrates are suspended in a solvent, preferably water, and solutions of the metal salts of a) Ti and b) Al, Mg or Ca and c) Si and d) Zn are added. The oxides, hydroxides and/or oxide hydrates are precipitated onto the substrates here, with the substrates being sheathed. For rutilisation of the titanium dioxide present in the outer coating according to the invention, a tin dioxide layer can usually be applied between substrate and outer coating according to the invention. Suitable starting compounds for the oxides, hydroxides and/or oxide hydrates to be precipitated are the corresponding halides, nitrates and/or sulfates, the corresponding halides and/or nitrates are preferably employed. The oxides, hydroxides and/or oxide hydrates of silicon are preferably applied by means of a silane, in particular TEOS (tetraethoxysilane). The metal salt solutions are added simultaneously or successively at a pH which is suitable for hydrolysis of the salts, where the pH is selected so that the metal oxides or hydroxides or oxide hydrates are deposited directly on the substrates. The Ti and Al (or Mg or Ca) salt solutions can preferably be metered in simultaneously, where some of the Ti salt solution can also be added alone at the beginning. The Si and Zn salt solutions can also be added simultaneously. However, it is also possible to add the Si salt solution first and then the Zn salt solution or vice versa. It is also possible to add the Zn salt solution first, then to add Al salt solution and then the Si salt solution. The Al and Si salt solutions can then preferably be metered in simultaneously. The pH is usually kept constant by simultaneous metered addition of a base and/or acid. The adjustment of the pH necessary for the precipitation of the respective material and the temperature is familiar to the person skilled in the art.

After the wet-chemical application of the outer coating according to the invention, the substances can be in the form of oxides, hydroxides and/or oxide hydrates. The following amounts of the elements mentioned under a) to d) which are essential to the invention are preferably precipitated onto the substrates as oxides, hydroxides and/or oxide hydrates, based on the raw materials employed, where the amounts are indicated as oxides and the % by weight are based on the substrate: ≥1% by weight, preferably 1.5-12% by weight, in particular 2-12% by weight, of ZnO, ≥0.5, preferably 1-10% by weight, in particular 2-5% by weight, of $Al_2O_3$, MgO and/or CaO or mixtures of these metal oxides, preferably $Al_2O_3$, ≥2% by weight, preferably 1-15% by weight, in particular 2.5-8% by weight, of $SiO_2$ and ≥20% by weight, preferably ≥25% by weight, of $TiO_2$, where the precise $TiO_2$ content is dependent on the desired interference colour, and the adjustment is familiar to the person skilled in the art.

The coated products are subsequently separated off, washed, dried and calcined. The oxides, hydroxides and/or oxide hydrates formed during the wet-chemical application are thereby converted into the corresponding oxides and/or mixed oxides of the outer coating according to the invention. The drying can be carried out at temperatures of 50-150° C., usually for ≥10 minutes, if necessary for 6-18 hours. The calcination can be carried out at temperatures of 250-1000° C., preferably at 500-900° C., usually for 0.5-3 hours. Through the calcination, the precipitated oxides, hydroxides and/or oxide hydrates are dehydrated, converted into the corresponding oxides or mixed oxides and compacted.

After the calcination, if desired for specific applications, an organic coating can be applied to the outer metal oxide-containing, calcined coating. The coupling reagents are applied in solution at temperatures above 60° C., preferably above 70° C. Suitable solvents are organic solvents, water or mixtures thereof, water is preferably used. The reaction time necessary for the application of the organic coating is at least 5 minutes, it is preferably carried out over a period of 10 to 90 minutes, but can also be extended as desired. The pigment obtained is worked up and isolated by methods which are conventional for the person skilled in the art, for example by filtration, drying and sieving.

For the preparation of effect pigments according to the invention which have metal oxide-coated substrates beneath the outer coating which is essential to the invention, the outer coating which is essential to the invention can be applied to metal oxide-coated substrates, which may also have been calcined. However, such multilayered effect pigments according to the invention are preferably prepared in such a way that the metal oxide layers mentioned above, in particular the preferred metal oxide layers, which are on the substrate beneath the outer coating according to the invention, are applied directly before the application of the outer coating according to the invention, and the work-up is carried out by washing, drying and calcination in one step. In a particularly preferred embodiment of the invention, the outer coating according to the invention is applied to uncoated substrates, in particular comprising synthetic or natural mica.

An advantage of the effect pigments according to the invention is this simple preparation process, which makes no intermediate steps, such as, for example, drying and/or calcination and isolation of intermediates, necessary. Further advantages of the effect pigments according to the invention are low or no yellowing in the dark, low or no yellowing under UV irradiation and humidity with phenolic antioxidants (for example BHT), high light fastness and high weather stability.

The effect pigments according to the invention are thus particularly suitable for applications in the plastics sector, since they are preferably free from organic aftercoatings and are nevertheless weathering-stable, light fast, and low-yellowing and have low photoactivity. The storage stability of the pigments according to the invention may in addition be significantly increased. Furthermore, less yellowing in paints and plastics is observed on pigmentation with the effect pigments according to the invention. Owing to the improved applicational properties, the surface-modified effect pigments described here are suitable for a multiplicity of applications. The invention thus furthermore relates to the use of the effect pigments according to the invention in paints, coatings, in particular automotive paints, industrial coatings, powder coatings, printing inks, security applications, cosmetic formulations, plastics, ceramic materials, glasses, paper, in toners for electrophotographic printing processes, in seed, in greenhouse sheeting and tarpaulins, as absorbers in the laser marking of paper and plastics, as absorbers in the laser welding of plastics and in cosmetic formulations. In particular, the use of the effect pigments according to the invention in paints, in particular automotive paints, and the use in plastics is preferred. Furthermore, the pigments according to the invention are also suitable for the preparation of pigment pastes with water, organic and/or aqueous solvents, pigment preparations and for the preparation of dry preparations, such as, for example, granules, chips, pellets, briquettes, etc. The pigments can be incorporated into the respective application media by all methods known to the person skilled in the art.

The effect pigments according to the invention are preferably employed in paints, such as, for example, in automotive paints or water-borne paints, which, owing to the particular stability of the pigments, are suitable for all indoor and outdoor applications. All plastics and films known to the person skilled in the art can preferably advantageously be pigmented with the effect pigments in accordance with the present invention, where the pigments can be bound in both purely physically by mixing and also chemically by reaction of a corresponding functional group in the organic coating with the plastic. The effect pigments according to the invention are likewise suitable for use in blends with organic dyes and/or pigments, such as, for example, transparent and opaque white, coloured and black pigments, and with flake-form iron oxides, organic pigments, holographic pigments, LCPs (liquid crystal polymers) and conventional transparent, coloured and black lustre pigments based on metal oxide-coated flakes based on mica, glass, $Al_2O_3$, $Fe_2O_3$, $SiO_2$, etc. The effect pigments according to the invention can be mixed in any ratio with commercially available pigments and fillers.

Fillers which may be mentioned are, for example, natural and synthetic mica, nylon powder, pure or filled melanin resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances.

There are no restrictions regarding the particle shape of the filler. It can be, for example, flake-form, spherical or needle-shaped in accordance with requirements.

The disclosures in the references cited hereby expressly also belong to the disclosure content of the present application. The following examples explain the present invention in greater detail, without restricting the scope of protection. In particular, the features, properties and advantages, described in the examples, of the compounds and formulations on which the relevant examples are based can also be applied to other substances and compounds which are not mentioned in detail, but which fall within the scope of protection, unless stated otherwise elsewhere. The fine adjustment of the parameters mentioned in the examples is readily possible for the person skilled in the art in the individual case, for example by a statistical Box-Behnken experiment design, described in Statistics for Experimenters, Whiley-Interscience, John Whiley and Sons, New York, 1978. In addition, the invention can be carried out throughout the range claimed and is not restricted to the examples mentioned here.

EXAMPLES

Description of the Test Method for Testing Yellowing:

The yellowing of pigments arises principally in the presence of phenolic anti-oxidants on UV irradiation at high temperature and atmospheric humidity. In particular, inexpensive PE grades comprise BHT (2,6-di-tert-butyl-4-hydroxy-toluene) as antioxidant. This antioxidant forms yellow complex compounds with $TiO_2$. Pigmented, BHT-stabilised PE-HD plates are exposed to filtered xenon radiation in the Suntest XLS tester (Atlas). The visible changes are assessed using the grey scale in accordance with DIN EN 20105-A02. Injection-moulded plates made from Hostalen GA 7260 (PE-HD), which comprise 1% by weight of the pigment to be tested and 0.3% of BHT, are used. BHT is metered in in the form of a masterbatch of 1% of butylhydroxytoluene (Merck Schuchardt) in Hostalen GA 7260. The sample space is flooded with water, so that the plates are completely covered with water.

For sampling, the plates are briefly removed from the apparatus, dried off, assessed visually. The sampling is carried out under a daylight lamp. Sampling after 250 h. The assessment scale extends from 5 (very good) to 1 (very poor).

Description of the Test Method for Light Stability:

It is in fact not sensible to speak of "light stability of pigments", since no pigment is usually employed in practice without binders (binder, plastic or the like). However, as soon as pigments are used together with binders/plastics, it is not the light stability of pigments that is determined, but instead that of the system as a whole—pigment+binder+additives. References to the "light stability of pigments" are therefore always system-dependent. The light stability of pigments in the above-mentioned sense is tested in injection-moulded PE-HD plates having a thickness of 1.5 mm and at a pigment concentration of 1 part by weight. The PE-HD plates are exposed in the Xenotest 150 S (Atlas, filter system: "exposure outdoors" 1 UV filter+6 IR filters) compared with the blue scale (DIN EN ISO 105-B01). The colour changes of the exposed surfaces against the unexposed surfaces of the injection mouldings are assessed in accordance with the grey scale (DIN EN 20105-A02). The light stability here is defined as the step of the blue scale at which an irreversible change of 4 or more (i.e. 3, 2 . . . ) has occurred both at the specular angle (with virtually perpendicular viewing) in reflected light, and also in transmitted light. Changes which can be observed at other viewing directions are not taken into consideration here. The assessment scale extends from 8 (very good) to 1 (very poor).

Description of the Test Method for Weathering Stability

The samples are tested in order to test the weathering in PMMA in accordance with DIN 11341 for 1000 h. The samples consist of injection-moulded Plexiglas 7N comprising 1% by weight of pigment and are weathered in the Xenotest Beta+(Atlas) in accordance with DIN 11341 for 1000 h. The assessment scale extends from 5 (very good) to 1 (very poor).

Procedure for Testing the Photoactivity

The photoactivity test allows characterisation of the photocatalytic efficacy of $TiO_2$ or $TiO_2$-containing pigments. The test medium used is a PVC mixture comprising $Pb^{2+}$ salts and glycerol monooleate as reactants. During the test, $Pb^{2+}$ ions are reduced to Pb under the influence of the photoactive $TiO_2$, which can be observed macroscopically as greying. The greying of the samples is assessed in accordance with the DIN 54001 grey scale within 2 h of the end of the test (storage at room temperature). The assessment scale extends from 5 (very good) to 1 (very poor).

Example 1

100 g of natural mica flakes having a particle size of 10-60 µm are suspended in 1 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) of 72 g of $TiCl_4$ is metered in, during which the pH is held at pH 1.8 by addition of dilute sodium hydroxide solution. Sufficient solution is metered in over the course of 6 hours that the calcined pigment comprises 30% by weight of $TiO_2$ and exhibits silver-white interference. When approximately half of the $TiCl_4$ solution has been metered in, an aqueous solution of 9.5 g of $AlCl_3 \times 6H_2O$ (2% by weight solution) is metered in for the remaining 3 hours in parallel to the $TiCl_4$ solution. The pH is then adjusted to pH 7 using dilute hydrochloric acid, and a solution of 6.7 g of zinc chloride+1.2 g of 37% by weight HCl+80 g of deionised water is added over the course of one hour. 21 g of TEOS (tetraethoxysilane, 25% by weight alcoholic solution) is added over the course of 30 minutes, the mixture is stirred for a further 30 minutes, and the pH is then adjusted to pH 6 over the course of 60 minutes.

The suspension is worked up. The pigment is filtered off, washed, dried, calcined at 900° C. and subsequently sieved. The calcined pigment comprises 30% by weight of titanium dioxide, 1.2% by weight of ZnO and in addition to the content of $Al_2O_3$ and $SiO_2$ in the mica +3% by weight of aluminium oxide, and +3% by weight of silicon dioxide. Example 1 represents an interference silver, which normally has a layer thickness of the $TiO_2$ layer of 50-60 nm per side of the substrate. The layer thickness measured here of the outer coating according to the invention is about 90 nm per side of the substrate. This is an increase in the layer thickness by 50-80%.

Example 2

100 g of natural mica flakes having a particle size of 10-60 μm are suspended in 1 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) of 72 g of $TiCl_4$ is metered in, during which the pH is held at pH 1.8 by addition of dilute sodium hydroxide solution. Sufficient solution is metered in over the course of 6 hours that the calcined pigment comprises 30% by weight of $TiO_2$ and exhibits silver-white interference. When the $TiCl_4$ solution has been metered in, the mixture is stirred for a further 30 minutes. The pH is then adjusted to pH 7 using dilute sodium hydroxide solution, and a solution of 5 g of zinc chloride+0.9 g of 37% by weight HCl+60 g of deionised water is added over the course of one hour, and the mixture is stirred for a further 30 minutes. An aqueous solution of 9.5 g of $AlCl_3 \times 6H_2O$ (2% by weight solution) is then metered in over 30 minutes. The mixture is subsequently stirred for a further 30 minutes. 28 g of TEOS (tetraethoxysilane, 25% by weight alcoholic solution) is added over the course of 30 minutes at pH 7, the mixture is stirred for a further 30 minutes, and the pH is then adjusted to pH 6 over the course of 60 minutes. The suspension is worked up. The pigment is filtered off, washed, dried, calcined at 900° C. and subsequently sieved. The calcined pigment comprises 30% by weight of titanium dioxide, 0.9% by weight of ZnO and in addition to the content of $Al_2O_3$ and $SiO_2$ in the mica +3% by weight of aluminium oxide, and +4% by weight of silicon dioxide. Example 2 represents an interference silver, which normally has a layer thickness of the $TiO_2$ layer per side of substrate of 50-60 nm. The layer thickness measured here of the outer coating according to the invention is about 90 nm per side of the substrate. This is an increase in the layer thickness by 50-80%.

Example 3

100 g of natural mica flakes having a particle size of 10-60 μm are suspended in 2 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) of 72 g of $TiCl_4$ is metered in, during which the pH is held at pH 1.8 by addition of dilute sodium hydroxide solution. Sufficient solution is metered in over the course of 6 hours that the calcined pigment comprises 30% by weight of $TiO_2$ and exhibits silver-white interference. When approximately half of the $TiCl_4$ solution has been metered in, 100 ml of an aqueous solution of $CaCl_2$ (14.4 g of $CaCl_2 \times 2 H_2O$ +12 ml of a 30% $H_2O_2$ solution made up to 100 ml with water) are metered in for the remaining 3 hours in parallel to the $TiCl_4$ solution, and the mixture is then stirred for a further 30 minutes. The pH is subsequently adjusted to pH 7 using dilute sodium hydroxide solution, and a solution of 5 g of zinc chloride+0.9 g of 37% by weight HCl+60 g of deionised water is added over the course of one hour, and the mixture is stirred for a further 30 minutes. 28 g of TEOS (tetraethoxysilane, 25% by weight alcoholic solution) is added over the course of 30 minutes at pH 7, the mixture is stirred for a further 30 minutes, and the pH is then adjusted to pH 6 over the course of 60 minutes.

The suspension is worked up. The pigment is filtered off, washed, dried, calcined at 900° C. and subsequently sieved. The calcined pigment comprises 30% by weight of titanium dioxide, 0.9% by weight of ZnO, 3% by weight of calcium oxide and in addition to the content of $SiO_2$ in the mica +4% by weight of silicon dioxide. Example 3 represents an interference silver, which normally has a layer thickness of the $TiO_2$ layer of 50-60 nm per side of the substrate. The layer thickness measured here of the outer coating according to the invention is about 90 nm per side of the substrate. This is an increase in the layer thickness by 50-80%.

Example 4

100 g of synthetic mica flakes having a particle size of 10-40 μm are suspended in 2 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) comprising approximately 72 g of $TiCl_4$ is metered in, during which the pH is held at pH 1.8 by addition of dilute sodium hydroxide solution. Sufficient solution is metered in over the course of 6 hours that the calcined pigment comprises 30 by weight of $TiO_2$ and exhibits silver-white interference. When approximately half of the $TiCl_4$ solution has been metered in, 100 ml of an aqueous solution of $CaCl_2$ (14.4 g of $CaCl_2 \times 2 H_2O$ +12 ml of a 30% $H_2O_2$ solution made up to 100 ml with water) are metered in for the remaining 3 hours in parallel to the $TiCl_4$ solution. The pH is subsequently adjusted to pH 5 using dilute sodium hydroxide solution, and a solution of 5 g of zinc chloride+0.9 g of 37% by weight HCl+60 g of deionised water is added over the course of one hour. 28 g of TEOS (tetra-ethoxysilane, 25% by weight alcoholic solution) is added over the course of 30 minutes at pH 7, the mixture is stirred for a further 30 minutes, and the pH is then adjusted to pH 6 over the course of 60 minutes.

The suspension is worked up. The pigment is filtered off, washed, dried, calcined at 900° C. and subsequently sieved. The calcined pigment comprises 30% by weight of titanium dioxide, 0.9% by weight of ZnO and in addition to the content of CaO and $SiO_2$ in the mica +1.3% of CaO +4% by weight of silicon dioxide. Example 4 represents an interference silver, which normally has a layer thickness of the $TiO_2$ layer of 50-60 nm per side of the substrate. The layer thickness measured here of the outer coating according to the invention is about 90 nm per side of the substrate. This is an increase in the layer thickness by 50-80%.

Example 5

100 g of $SiO_2$ flakes having a particle size of 10-40 μm are suspended in 2 l of water and heated to 75° C. with stirring. An aqueous 10% by weight solution of 3.35 g of $SnCl_4$ is metered into the suspension over the course of one hour, during which the pH is held at 2.2 by addition of dilute sodium hydroxide solution, and the mixture is stirred for a further 30 minutes. An aqueous solution (30% by weight solution) of 72 g of $TiCl_4$ is metered in, during which the pH is held at pH 1.8 by addition of dilute sodium hydroxide solution. Sufficient solution is metered in over the course of 6 hours that the calcined pigment comprises 30% by weight of $TiO_2$ and exhibits silver-white interference. When approximately 90% of the $TiCl_4$ solution has been metered in, the pH is adjusted to 2.0, and the metering rate is slowed to half. A solution of 28 g of TEOS (tetraethoxysilane, 12% by weight alcoholic solution) is then metered in in parallel to the $TiCl_4$ solution, and an aqueous solution of 9.5 g of $AlCl_3 \times 6H_2O$ (1% by weight solution) is added for the remaining 1.2 hours, and the mixture is stirred for a further 10 minutes. A solution of 5 g of zinc chloride+0.9 g of 37% by weight HCl+60 g of deionised water is subsequently added, the mixture is stirred for a further 30 minutes.

The suspension is worked up. The pigment is filtered off, washed, dried, calcined at 900° C. and subsequently sieved. The calcined pigment comprises 30% by weight of titanium dioxide, 0.9% by weight of ZnO, 3% by weight of aluminium oxide and in addition to the content of $SiO_2$ in the mica +4% by weight of silicon dioxide. Example 5 represents an interference silver, which normally has a layer thickness of the $TiO_2$ layer of 50-60 nm per side of the substrate. The layer thickness measured here of the outer coating according to the invention is about 90 nm per side of the substrate. This is an increase in the layer thickness by 50-80%.

Example 6

Reference I 100 g of mica flakes having a particle size of 10-60 μm are suspended in 1 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) of 72 g of $TiCl_4$ is metered in over the course of 6 hours, during which the pH is held at 1.8 by addition of dilute sodium hydroxide solution. The mixture is subsequently stirred for a further 30 minutes. The pH is then adjusted to pH 6 using dilute hydrochloric acid. The suspension is worked up. The pigment is filtered off, washed, dried, calcined at 900° C. and subsequently sieved. The calcined pigment comprises 30% by weight of titanium dioxide. Example 6 represents an interference silver, which has a layer thickness of the $TiO_2$ layer of about 50 nm per side of the substrate.

Example 7

Reference II 100 g of mica flakes having a particle size of 10-60 μm are suspended in 1 l of water and heated to 75° C. with stirring. An aqueous 10% by weight solution of 3.35 g of $SnCl_4$ is metered into the suspension over the course of one hour, during which the pH is held at 1.8 by addition of dilute sodium hydroxide solution, and the mixture is stirred for a further 30 minutes. An aqueous solution (30% by weight solution) of 72 g of $TiCl_4$ is metered in over the course of 6 hours, during which the pH is held at 1.8 by addition of dilute sodium hydroxide solution. When half of the $TiCl_4$ solution, an aqueous solution of 9.5 g of $AlCl_3 \times 6H_2O$ is metered in for the remaining 3 hours in parallel to the $TiCl_4$ solution. The mixture is subsequently stirred for a further 30 minutes. The pH is then adjusted to pH 6 using dilute hydrochloric acid.

The suspension is worked up. The pigment is filtered off, washed, dried, calcined at 900° C. and subsequently sieved. The calcined pigment comprises 30% by weight of titanium dioxide. Example 7 represents an interference silver, which has a layer thickness of the $TiO_2$ layer of about 50 nm per side of the substrate.

The results of the test experiments are shown in Table 1. The pigments of Examples 1 and 2 according to the invention exhibit significantly better stability and lower porosity than a pigment of the prior art. In addition, the BET surface area (measured in accordance with DIN ISO 9277: 2003-05) in Example 1 is reduced by 63% and in Example 2 by 69% compared with reference I (Example 6).

TABLE 1

| Examples of mica having a particle size of 10-60 μm or 10-40 μm | | | | |
|---|---|---|---|---|
| Example | BET (calcination at 900° C.) | Light stability | Photoactivity | Yellowing |
| Reference I | 6.5 m²/g | 6 | 2-1 | 1 |
| Reference II | 4.2 m²/g | 6-7 | 2-1 | 1 |
| 1 | 2.4 | 8 | 4 | 3 |
| 2 | 2.0 | 8 | 3 | 4 |
| 3 | 2.3 | 8 | 3 | 4 |
| 4 | 3.0 | 8 | 3 | 4 |

The invention claimed is:

1. Effect pigments having a corresponding interference color
based on substrates A) or B), which substrates are
   A) uncoated, flake-form substrates or
   B) flake-form substrates coated with one or more metal oxides,
said effect pigments comprising on the substrates A) or B) an outer metal oxide-containing, calcined coating comprising
   a) $TiO_2$ and
   b) $Al_2O_3$, MgO and/or CaO, and
   c) $SiO_2$ and
   d) ZnO,
   or
   e) comprising a) to d), but wherein some or all of a) to d) are present in at least one mixed oxide form instead of their form in a) to d),
wherein of the metal oxide-containing, calcined outer coating has a thickness that is ≥20% more than a physical layer thickness of the corresponding interference colour.

2. Effect pigments according to claim 1, wherein the outer coating consists of
a) $TiO_2$ and
b) $Al_2O_3$, MgO and/or CaO, and
c) $SiO_2$ and
d) ZnO,
or
e) consisting of a) to d), but wherein some or all of a) to d) are present in at least one mixed oxide form instead of their form in a) to d).

3. Effect pigments according to claim 1, wherein the outer coating consists of
a) $TiO_2$ and
b) $Al_2O_3$ and
c) $SiO_2$ and
d) ZnO,
or
e) consisting of a) to d), but wherein some or all of a) to d) are present in at least one mixed oxide form instead of their form in a) to d).

4. Effect pigments according to claim 1, which have been calcined, and which comprise ≥20% by weight of $TiO_2$, ≥0.5% by weight of ZnO, ≥0.1% by weight of $Al_2O_3$ and ≥1.5% by weight of $SiO_2$ in the outer coating, where the % by weight are based on the total weight of the calcined pigment.

5. Effect pigments according to claim 1, which have a specific surface area which is reduced by 30-80% compared with the specific surface area of a pigment comprising a calcined $TiO_2$ layer as outer layer.

6. Effect pigments according to claim 1, wherein the flake-form substrates A) are selected from the group consisting of flakes of synthetic mica, flakes of natural mica, glass flakes, $SiO_2$ flakes and $Al_2O_3$ flakes.

7. Effect pigments according to claim 1, wherein the flake-form substrates B) are coated with oxides and/or oxide hydrates of aluminium, silicon, iron, tin or titanium or a mixture thereof.

8. Effect pigments according to claim 1, which have been calcined, and wherein the outer coating of the calcined pigment has a thickness of ≥50 nm.

9. Effect pigments according to claim 1, wherein the thickness of the outer coating is ≥40% more than the physical layer thickness of the corresponding interference colour.

10. Effect pigments according to claim 1, wherein the thickness of the outer coating is 50-80% more than the physical layer thickness of the corresponding interference colour.

11. Effect pigments according to claim 1, wherein the thickness of the outer coating is >100% more than the physical layer thickness of the corresponding interference colour.

12. Effect pigments according to claim 1, wherein the outer coating comprises
a) $TiO_2$ and
b) $Al_2O_3$, MgO and/or CaO, and
c) $SiO_2$ and
d) ZnO.

13. Effect pigments according to claim 1, which have a specific surface area of ≤4 $m^2/g$, measured by the BET method (DIN ISO 9277: 2003-05).

14. Effect pigments according to claim 1, which have a specific surface area of ≤3 $m^2/g$, measured by the BET method (DIN ISO 9277: 2003-05).

15. A process for preparing effect pigments according to claim 1, comprising
a) applying an outer coating to the substrates A) or B), which outer coating is of
Ti and
Zn and
Al, Mg and/or Ca, and
Si
oxides, hydroxides and/or oxide hydrates by a wet-chemical method, and
b) then working up, and thereafter calcining the flake form substrates.

16. A process according to claim 15, comprising suspending the substrates in an aqueous solution, adding a
Ti, and
Si, and
Zn and
Al, Mg and/or Ca
salt solution at a pH which is suitable for hydrolysis of the salts, and where the pH is selected so that the metal oxides or hydroxides or oxide hydrates are deposited on the substrates.

17. A process according to claim 15, wherein
a) Ti and
b) Al, Mg and/or Ca,
salt solutions are metered in simultaneously, where some of the Ti salt solution is optionally also added alone at the beginning.

18. A process according to claim 15, wherein firstly a Ti salt solution, then a Zn salt solution, then a Al salt solution and then a Si salt solution are added.

19. A process according to claim 15, wherein Si and Al salt solutions are added simultaneously.

20. Effect pigments prepared by a process according to claim 15.

21. A product selected from the group consisting of paints, coatings, automotive paints, powder coatings, printing inks, security printing inks, plastics, ceramic materials, glasses, paper, paper coating, toners for electrophotographic printing processes, seed, greenhouse sheeting, tarpaulins, absorbers in the laser marking of paper and plastics, absorbers in the laser welding of plastics, cosmetic formulations, pigment pastes with water, organic solvents, aqueous solvents, pigment preparations and dry preparations, comprising effect pigments according to claim 1.

* * * * *